US008894978B2

(12) United States Patent
Prendergast

(10) Patent No.: US 8,894,978 B2
(45) Date of Patent: *Nov. 25, 2014

(54) SYSTEM AND METHOD OF COMPLIMENTARY DAY/NIGHT CHILDREN'S SKIN CREAM COMPOSITIONS

(71) Applicant: William Scott Prendergast, Leesburg, VA (US)

(72) Inventor: William Scott Prendergast, Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,165

(22) Filed: Apr. 25, 2014

(65) Prior Publication Data

US 2014/0234236 A1 Aug. 21, 2014

Related U.S. Application Data

(63) Continuation of application No. 13/310,455, filed on Dec. 2, 2011, now Pat. No. 8,747,817.

(60) Provisional application No. 61/418,940, filed on Dec. 2, 2010.

(51) Int. Cl.

| | | |
|---|---|---|
| *A61Q 17/04* | (2006.01) | |
| *A61K 33/30* | (2006.01) | |
| *A61K 31/355* | (2006.01) | |
| *A61K 36/886* | (2006.01) | |
| *A61K 36/45* | (2006.01) | |
| *A61K 36/30* | (2006.01) | |
| *A61K 36/28* | (2006.01) | |
| *A61K 31/315* | (2006.01) | |
| *A61K 47/44* | (2006.01) | |
| *A61K 8/97* | (2006.01) | |
| *A61Q 19/04* | (2006.01) | |
| *A61K 8/34* | (2006.01) | |
| *A61K 8/60* | (2006.01) | |
| *A61K 8/67* | (2006.01) | |
| *A61K 8/96* | (2006.01) | |
| *A61Q 19/00* | (2006.01) | |

(52) U.S. Cl.
CPC . *A61K 8/97* (2013.01); *A61Q 17/04* (2013.01); *A61Q 19/04* (2013.01); *A61K 33/30* (2013.01); *A61K 36/28* (2013.01); *A61K 36/45* (2013.01); *A61K 36/886* (2013.01); *A61K 36/30* (2013.01); *A61K 8/34* (2013.01); *A61K 8/60* (2013.01); *A61K 8/678* (2013.01); *A61K 8/96* (2013.01); *A61Q 19/00* (2013.01)
USPC .......... 424/59; 424/283.1; 424/642; 424/725; 424/732; 424/744; 514/458; 514/494; 514/782

(58) Field of Classification Search
None
See application file for complete search history.

(56) References Cited

U.S. PATENT DOCUMENTS

| | | | |
|---|---|---|---|
| 5,256,649 A | * | 10/1993 | Le Fur et al. .................. 514/46 |
| 5,876,737 A | | 3/1999 | Schonrock et al. |
| 7,195,787 B1 | * | 3/2007 | Pykett et al. .................. 424/728 |
| 7,416,719 B2 | | 8/2008 | Huerta et al. |
| 8,048,456 B2 | | 11/2011 | Burke-Colvin et al. |
| 2004/0005278 A1 | | 1/2004 | Reinhart et al. |
| 2004/0180102 A1 | | 9/2004 | Patt |
| 2004/0228824 A1 | | 11/2004 | Voigt et al. |
| 2007/0020216 A1 | | 1/2007 | Reinhart et al. |
| 2007/0104662 A1 | | 5/2007 | Satonaka et al. |
| 2007/0172431 A1 | | 7/2007 | Galumbeck |
| 2007/0218021 A1 | | 9/2007 | Wells |
| 2008/0025932 A1 | | 1/2008 | Bissett et al. |
| 2008/0199489 A1 | | 8/2008 | Parrincello |
| 2008/0213300 A1 | | 9/2008 | Jochim et al. |
| 2009/0018200 A1 | | 1/2009 | Willemin et al. |
| 2009/0028897 A1 | * | 1/2009 | Maestro et al. .......... 424/195.16 |
| 2009/0035237 A1 | | 2/2009 | Maes et al. |
| 2009/0041691 A1 | | 2/2009 | Candau et al. |
| 2009/0068132 A1 | | 3/2009 | Bratescu et al. |
| 2009/0074822 A1 | | 3/2009 | Declerq et al. |
| 2009/0117061 A1 | | 5/2009 | Gross |
| 2009/0130029 A1 | | 5/2009 | Tamarkin et al. |
| 2009/0169588 A1 | | 7/2009 | Beutler et al. |
| 2010/0048737 A1 | | 2/2010 | Wendel et al. |
| 2010/0080845 A1 | | 4/2010 | Maes et al. |
| 2010/0086502 A1 | | 4/2010 | Lucet-Levannier et al. |
| 2010/0104523 A1 | | 4/2010 | Wagner et al. |
| 2010/0112100 A1 | | 5/2010 | Willemin et al. |

(Continued)

FOREIGN PATENT DOCUMENTS

WO   WO 01/17495 A1 * 3/2001 ............... A61K 7/42

OTHER PUBLICATIONS

U.S. Patent Documents—None.*
Google Search; two pages; downloaded Sep. 3, 2014.*

(Continued)

*Primary Examiner* — Jeffrey T Palenik
(74) *Attorney, Agent, or Firm* — Symbus Law Group, LLC; Clifford D. Hyra

(57) ABSTRACT

A new skin care system includes day and night skin cream compositions comprising nutrients and antioxidants for use by children between six months and eighteen years of age. The day skin cream composition provides protection from UV radiation and the night skin cream composition contains no sun protection ingredients and elevated levels of nutrients and antioxidants. A child-friendly bottle for each composition can be used by young children without difficulty. A fragrance included in each composition is popular with children, and the bottle for the day composition has graphics indicating day-time use and the bottle for the night composition has graphics indicating night-time use. The day composition is applied topically each day to the face after tooth-brushing, and the night composition is applied topically to the face each night after tooth-brushing.

6 Claims, No Drawings

(56) References Cited

U.S. PATENT DOCUMENTS

| | | |
|---|---|---|
| 2010/0158825 A1 | 6/2010 | Maesen et al. |
| 2010/0172944 A1 | 7/2010 | Laboureau et al. |
| 2012/0087996 A1 | 4/2012 | Palmer |

OTHER PUBLICATIONS

Google Scholar Search; two pages; downloaded Sep. 3, 2014.*

Skin Function and Development, Children's Environmental Health Project, printed Nov. 3, 2013, available at www.cape.ca/children/derm1.html.

Adult Skin vs. Baby Skin, Johnson & Johnson Consumer Companies, Inc., printed Nov. 3, 2013, available at www.desitin.com/adult-skin-vs-baby-skin.html.

Young Skin vs. Old Skin, Natural Skin Care Info and Tips, printed Nov. 3, 2013, available at naturalskincareinfoandtips.blogspot.com/2013/04/young-skin-vs-old-skin.html.

Children's Skin: The special characteristics of babies' and children's skin, SebaPharma, printed Nov. 3, 2013, available at www.sebamed.com/my-skin.childrens-skin.html.

How Does Infant Skin Differ from Adult Skin?, Peter Lio, MD, Jun. 20, 2011, available at www.medscape.org/viewarticle/743529_print.

Skin Care for Infants and Young Children: Using New Evidence to Address Common Myths, SHerrill J. Rudy, Jun. 20, 2011, available at www.medscape.org/viewarticle/743532_print.

* cited by examiner

SYSTEM AND METHOD OF COMPLIMENTARY DAY/NIGHT CHILDREN'S SKIN CREAM COMPOSITIONS

This application claims the benefit of U.S. application Ser. No. 13/310,455 filed Dec. 2, 2011, which claims priority to Provisional Application No. 61/418,940, filed Dec. 2, 2010, which is hereby incorporated by reference herein.

BACKGROUND

The present invention relates generally to skin care and cosmetic compositions therefor, and more particularly to systems of complementary skin care products designed specifically for children.

Skin damage accumulates over a lifetime, beginning during infancy and building over childhood and adulthood until the cumulative effects result in serious diseases and disorders like skin cancer and/or serious aesthetic and functional damage to the skin. The main effect of sun damage and neglect, other than hyper-pigmentation and cancer, is to seriously degrade a person's appearance over time.

Children's skin differs from that of adults and changes over the course of childhood. Infant skin is softer and more prone to irritation and loss of moisture, while older children are prone to acne. It is difficult to get children to follow personal care regimens. Children may not like the appearance, smell, etc. of adult products, which also may not be properly formulated for children and can be harmful to them. Children may lack the motor skill or motivation to follow more complex or time-consuming care regimens.

Needs exist for improved skin care formulations, systems, and methods.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

A new skincare system and method utilizes complementary day and night skin cream formulations designed specifically for use by children ages six months to eighteen years. The complementary creams work together to produce a result greater than would be achieved by using either one separately or in conjunction with different products. The creams are formulated without harsh chemicals that could be damaging to the skin of young children and with largely natural ingredients. They and their packaging are designed to have an appearance, feel and scent that is attractive to children across a wide age range and are designed for a simple method of use that works within the existing personal care habits of children. The use of this system and method prevents the accumulation of skin damage over childhood, greatly improving the health and appearance of the skin over the user's lifetime.

A new system includes day and night skin cream compositions comprising nutrients and antioxidants for use by children between six months and eighteen years of age. The day skin cream composition provides protection from UV radiation and the night skin cream composition contains no sun protection ingredients and elevated levels of nutrients and antioxidants.

In one embodiment, there is a child-friendly bottle for each composition that can be used by young children without difficulty, both compositions include deionized water, capric triglyceride, shea butter, sunflower seed oil, vegetable glycerin, borage seed oil, cetearyl alcohol and glucoside, glyceryl stearate, xanthan gum, benzyl alcohol, fragrance, Vitamin E, aloe vera barbadensis leaf juice, and blueberry extract, the day composition also includes zinc oxide and T-lite SF-S and has an SPF of at least 20, and the nighttime composition also includes stearic acid. The fragrance is popular with children, and the bottle for the day composition has graphics indicating day-time use and the bottle for the night composition has graphics indicating night-time use.

In a new method of using the new system, the day composition is applied topically in the morning and the night composition is applied topically at night. In one embodiment, the day composition is applied topically each day to the face after tooth-brushing, and the night composition is applied topically to the face each night after tooth-brushing.

These and other objectives and features of the invention are apparent in the disclosure, which includes the above and ongoing written specification.

DETAILED DESCRIPTION

A complementary day/night skin cream system formulation and method will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

Skin is the largest organ of the human body and plays a vital role in preventing infection, protecting the body from radiation, physical trauma, and other environmental hazards, and otherwise maintaining the health of an individual. Of course, skin also presents the outward appearance of a person, and as such is critical to others' perceptions of a person as youthful, beautiful, etc.

The skin protects the rest of the human body by shielding it and absorbing the damaging effects of physical and environmental trauma. As such, over time the skin tends to accumulate damage and to degrade, as well as to naturally age, developing wrinkles, unattractive marks including scars, blemishes, and hyper-pigmentation, and potentially cancerous cells, and losing elasticity and moisture.

However, skin health can be maintained in part by application of appropriate topical compositions, including moisturizers and nutrients, which are absorbed into the skin, as well as by proper diet and exercise. Sunscreens help to prevent sun damage, a major cause of skin deterioration. While skin heath tends to be of greatest concern to aging people and to women, in fact skin health is of great importance to people of all ages and races and to both men and women. The accumulation of skin damage begins in childhood. Therefore, to best maintain healthy skin over a lifetime, skin maintenance should begin during childhood.

A new skin care system and method uses daytime and nighttime formulations and is designed for children from 6 months to 18 years of age, for daily and nightly use to protect the skin from sun damage and maintain skin health. In specific embodiments, the daytime formulation is SPF 21.33 and also includes ingredients to nourish the skin and the nighttime formulation has extra antioxidants to overnourish the skin. The formulations have a consistency, feel, and smell that children like. Daytime formulation ingredients include deionized water, capric triglyceride, shea butter, sunflower seed oil, vegetable glycerin, borage seed oil, cetearyl alcohol and glucoside, glyceryl stearate, xanthan gum, benzyl alcohol, fragrance, Vitamin E, aloe vera barbadensis leaf juice, blueberry extract, zinc oxide, and T-lite SF-S. Nighttime formulation ingredients include the same, with the exception of z-cote and T-lite SF-S (sunscreen ingredients) and the addition of stearic acid, although in differing concentrations. In some embodiments, the nighttime formulation also includes sweet almond oil, cucumber extract, and acai berry extract. In some embodiments, the nighttime formulation also includes coffee bean extract.

This system starts with children at a young age and teaches them how to take care of their skin and the importance of skin health. Instead of trying to undo the effects of age and sun damage after they have occurred, this system slows the skin's aging process and prevents environmental damage from occurring in the first place. The two-step system of complementary day and night formulations ensures that the optimal formulation is being used at all times. The daytime formulation has SPF factors as well as other skin nutrients, but the nighttime formulation has a much stronger concentration of antioxidants and moisturizers, and does not have the SPF ingredients.

Typically, sunscreen is applied only during high sun activities such as the beach, pool, etc. While some cosmetics include some SPF protection, generally males do not use such products, and neither do children. Sun damage accumulates on a daily basis from everyday activities like driving or riding in a car, walking to school or to lunch, playing outside, such as at recess, etc. This is when the majority of sun exposure and sun damage occurs.

In this new daily skin care regimen, the day/night system is applied in the morning before leaving the house and at night when the sun is down and/or the child will not be leaving the house. The formulations are applied topically to the user's face, which is rarely covered by clothing and typically accumulates the most damage, yet is also the most critical to appearance. The formulations may also be applied to other vulnerable areas, such as the backs of the hands or forearms. The day formulation includes SPF for protection against sun damage, while the night formula does not, instead having a stronger concentration of nutrients. Nutrients such as vitamins and antioxidants improve overall skin health and help prevent or repair damage from the sun and from free radicals, maintaining skin elasticity and preventing the development of lines and wrinkles.

The system makes sense and is extremely practical. The high-antioxidant night créme can be applied by a child in approximately 10 seconds after they brush their teeth at night, and the moderate-SPF day formulation can be applied in the morning after they brush. This provides great skin nourishment and protection to give the user more beautiful skin and protect against one of the fastest occurring cancers today, skin cancer.

This first daily skin care regimen for children protects, hydrates, and helps prevent skin damage and premature aging. After years of research and development, the formulations have been optimized to provide the very best skin care for youths of all ages. The system delivers protection, hydration, and prevention (PHP) in one simple process utilizing the very best ingredients.

In certain embodiments, various features of the formulations ensure their attractiveness to children. Scents which have been shown in testing to be popular scents with children are applied to the formulations to ensure that a majority of children like the scent, which is an important factor in getting children to use a product, much more so than for adults. For the nighttime formula graphics of moons and stars are attractive and provide an immediate indication that the product is for bedtime use. For the daytime formula, graphics of the sun provide an immediate indication that the daytime formula is to be used at the start of each day. The bottles are kid-friendly for easy self-application.

Because application is incorporated into existing morning/bedtime routines, the system becomes part of a child's way of life. Parents can educate their children on the importance of protecting their skin similarly to the importance of brushing their teeth at night before bedtime and when they awake. Establishing a habit of use is very important to delivering PHP for children.

Due to the complementary nature of the night and day creams, the night cream typically has substantially more water, more antioxidants and nutrients and less skin conditioning agents than the day cream, and unlike the day cream will have no sunscreen ingredients. It also typically requires a higher level of emulsifiers and the like for maintaining the product in solution in a desired texture and appearance. In certain embodiments, the day cream may have about 60% by weight water, about 30-35% skin conditioning agents, about 6% sunscreen ingredients, and less than 0.5% of antioxidant and nutrient-rich ingredients, all by weight. In contrast, the night cream may have about 75% water, 15-20% skin conditioning agents, and about 0.4% to 1% antioxidant and nutrient rich ingredients and no sunscreen ingredients. In certain embodiments, the day cream may have 50-65% water, 20-40% skin conditioning agents, 5-10% sunscreen ingredients, and less than 0.5% antioxidant and nutrient-rich ingredients, while the night cream may have 65-80% water, 10-20% skin conditioning agents, and 0.3 to 1.5% antioxidant and nutrient-rich ingredients. The pH of the night cream may be about 2.5 below that of the day cream. The pH of the day cream may in some embodiments be 7-8 and the pH of the night cream may be 4.5-5.5. The pH of the day cream may be in some embodiments 6.5-8.5 and the pH of the night cream may be 4-6.5.

Vitamin E, blueberry extract, and acai berry extract can generally be considered antioxidant and nutrient-rich ingredients, while cetearyl alcohol, stearate, xanthan gum, DHA and benzyl alcohol are emulsifiers, surfactants, or preservatives. Capric triglyceride, shea butter, sunflower seed oil, vegetable glycerol, borage seed oil, vitamin E, aloe barbadensis leaf juice, cucumber extract and sweet almond oil are skin conditioners.

Exemplary Formulations & Batching
Day Cream:

| Phase | Ingredient | % by WT |
|---|---|---|
| A | Deionized water | 58.5500 |
| B | Caprylic/Capric Triglyceride | 15.0000 |
| B | Shea Butter | 0.5000 |
| B | Sunflower Seed Oil | 8.0000 |
| A | Vegetable Glycerin 99.7% USP | 6.0000 |
| B | Borage Seed Oil | 2.5000 |

-continued

| Phase | Ingredient | % by WT |
|---|---|---|
| B | Cetearyl Alcohol and Cetearyl Glucoside | 0.5000 |
| B | Glyceryl Stearate | 0.5000 |
| C | Xanthan Gum | 0.5000 |
| D | Benzyl Alcohol/DHA | 1.0000 |
| D | Fragrance (Bell-Aire #40534) | 0.5000 |
| D | Tocopheryl Acetate (Vitamin E) | 0.1500 |
| D | *Aloe Vera Barbadensis* Leaf Juice | 0.1500 |
| D | Blueberry Extract | 0.1500 |
| B | Z-Cote (Zinc Oxide) | 3.0000 |
| B | T-Lite SF-S (Titanium Dioxide, Hydrated Silica, Dimethicone/Methicone Copolymer and Almuinum Hydroxide | 3.0000 |

Capric triglyceride is an oily liquid made from coconut oil that slows loss of water from the skin by forming a barrier on the skin's surface and alters the thickness of the solution. Shea butter, derived from the sheatree, is a skin conditioning agent and viscosity increasing agent that enhances the appearance of dry or damaged skin by reducing flaking and restoring suppleness and that slows the loss of water from the skin. Sunflower seed oil is a skin conditioning agent that enhances the appearance of dry or damaged skin by reducing flaking and restoring suppleness and that slows the loss of water from the skin. Vegetable glycerol is a sugar alcohol that increases the water content of the top layers of skin by drawing moisture from the surrounding air, and is also a skin protectant and viscosity decreasing agent. Borage seed oil is a plant seed oil that restores moisture and smoothness to dry and damaged skin and reduces inflammation. Cetearyl alcohol and cetearyl glucoside keep an emulsion from separating into its oil and liquid components. Glyceryl stearate acts as a lubricant on the skin's surface, giving the skin a soft and smooth appearance and slowing the loss of water from the skin by forming a barrier. It helps to form emulsions by reducing the surface tension of the substances that are emulsified. Xanthan gum is a binder, emulsion stabilizer, and surfactant and increases viscosity. Benzyl alcohol is a solvent, preservative, and viscosity decreasing agent. DHA is a preservative. Vitamin E is an antioxidant and helps to enhance the appearance of dry or damaged skin by reducing flaking and restoring suppleness. Aloe barbadensis leaf juice helps to enhance the appearance of dry or damaged skin by reducing flaking and restoring suppleness. Blueberry fruit extract contains many antioxidants and nutrients.

Batching:
1) Combine phase A and B separately while mixing and heat to 80-85° C.
2) When the oil phase (B) is totally melted, ensure that Z-Cote and T-Lite SF-S is mixed in.
Then sprinkle Xanthan Gum (phase C) into the oil phase.
3) Then add Phase A into Phase B/C. Continue to keep the temperature at 85° C.
4) Add back the water (q.s. to 100% by weight to replace water loss from heat)
5) Then homogenize the batch with the homogenizer (lab scale is approx. 3-5 minutes)
6) Switchback to mixing speed at low-medium speed
7) Turn heat off and continue mixing until it cools to 45-50° C.
8) Add Phase D (preservative and Aloe Vera juice)
9) Continue to mix until the batch is homogenous and temperature reaches 35-40° C. Stop mixer and evaluate.

The resulting product is an opaque emulsified lotion having a pH of 7.00-8.00, % solids of 38.4-42.4% (105 C, 1 hr), viscosity of 9,000-17,000 cps, and specific gravity of 0.940-1.040 gm/ml.

The most important aspect of the day cream is SPF protection. Sun damage is the single largest cause of skin cancer and of deleterious changes to skin appearance and most children are exposed to the sun daily when playing outside, being driven to activities, etc. The most sun damage accumulates in the face, where appearance is most important. This day cream is formulated to complement a night cream that over-nourishes the skin with large amounts of antioxidants and a low pH over night, freeing the day cream to contain high levels of sunscreen ingredients and resulting in a high SPF while maintaining a desirable appearance and texture and moisturizing properties.

Night Cream:

| Phase | Ingredient | % by WT |
|---|---|---|
| A | Deionized water | 76.5 |
| B | Caprylic/Capric Triglyceride | 4.5000 |
| B | Shea Butter | 0.7500 |
| B | Sunflower Seed Oil | 3.5000 |
| B | Stearic acid | 2.0000 |
| A | Vegetable Glycerin 99.7% USP | 4.0000 |
| B | Borage Seed Oil | 2.5000 |
| B | Cetearyl Alcohol and Cetearyl Glucoside | 2.0000 |
| B | Glyceryl Stearate | 1.5000 |
| C | Xanthan Gum | 0.9000 |
| E | Benzyl Alcohol/DHA | 0.5000 |
| D | Fragrance (Bell-Aire #40534) | 0.5000 |
| D | Tocopheryl Acetate (Vitamin E) | 0.1000 |
| D | *Aloe Vera Barbadensis* Leaf Juice | 0.1500 |
| D | Blueberry Extract | 0.1500 |
| D | Sweet Almond Oil | 0.1500 |
| D | Cucumber Melon Extract | 0.1500 |
| D | Acai Berry Extract | 0.1500 |

Stearic acid is a surfactant cleansing and emulsifying agent that cleans skin by helping water mix with oil and dirt so that they can be rinsed away and that helps to form emulsions by reducing surface tension. Cucumber melon extract is a skin conditioning agent that acts as a lubricant on the skin surface and gives the skin a soft and smooth appearance and enhances the appearance of dry or damaged skin by reducing flaking and restoring suppleness. Sweet almond oil acts as a lubricant on the skin surface, giving the skin a soft and smooth appearance. Acai berry extract contains a high level of antioxidants and nutrients.

Batching:
1) Add water and glycerin into main beaker. Turn mixer on until a vortex forms.
2) Sprinkle xanthan gum into the vortex. Increase the mixing speed as xanthan gum goes into solution.
3) Continue mixing until xanthan gum is free of clumps and homogenous
4) While mixing, in a separate beaker, add all the content of Phase B (oil phase)
5) Turn heat on and heat both phases up to 60-65° C.
6) Pour the content of oil phase (phase B) into phase A (main beaker)
7) Turn heat off and continue mixing until the main batch cools down to 40-45° C.
8) Then add the content of Phase D. Continue mixing.
9) Then add Phase E, preservative. Continue mixing for approx. 30 minutes or until the batch is homogenous. Stop mixer and take a sample for analysis.

The resulting product is an opaque emulsified lotion having a pH of 4.5-5.5, % solids of 20.7-22.9% (105 C, 1 hr), viscosity of 9,800-18,000 cps, and specific gravity of 0.910-1.000 gm/ml.

The night cream over-nourishes the skin with a high concentration of antioxidants and natural nutrients and moisturizes the skin overnight when the body tends to become dehydrated. Because it is for night use only, sunblock does not need to be included, and absorption of antioxidants and nutrients is greatest at night where the ingredients are less prone to deterioration due to exposure to the sun and the elements. Because it is designed to be used with a day cream having a high SPF and neutral pH, but lower levels of antioxidants, the night cream does not need high levels of ingredients to repair sun-damaged or very dry skin, but does need to supply a high level of antioxidants to provide extended protection for the user and has a low pH to rebuild and maintain the user's acid mantle (acidic layer) to protect against acne and other infections. Younger children may not have an acid mantle, and this low pH will help to counteract their greater susceptibility to infection. The cream also maintains the skin's proper moisture level.

The invention is not limited to the particular embodiments described above in detail. Those skilled in the art will recognize that other arrangements could be devised, for example, using various concentrations of the ingredients and using various ingredient substitutions, subtractions, or additions to achieve varying textures, etc. While the invention has been described with reference to specific illustrative embodiments, modifications and variations of the invention may be constructed without departing from the scope of the invention.

I claim:

1. A skin care composition for preventing damage to the skin of children, comprising:
  a day/night children's skin care system consisting of complementary day and night skin cream compositions comprising nutrients and antioxidants that are safe to be used by children between six months and eighteen years of age and are used in combination to protect against skin damage;
  wherein the day skin cream composition provides protection from UV radiation;
  wherein the night skin cream composition contains no sun protection ingredients and higher levels of water and nutrients and antioxidants than in the day skin cream composition;
  wherein the day skin cream composition comprises 50-65% water, 20-40% skin conditioning agents, 5-10% sunscreen ingredients, and less than 0.5% antioxidant and nutrient-rich ingredients by weight, and the night skin cream composition comprises 65-80% water, 10-20% skin conditioning agents, and 0.3 to 1.5% antioxidant and nutrient-rich ingredients by weight,
  wherein the night skin cream composition has a lower pH than the day skin cream composition.

2. The skin care system of claim 1, wherein the pH of the day skin cream composition cream is 6.5-8.5 and the pH of the night skin cream composition is 4-6.5.

3. The skin care system of claim 2, wherein the pH of the day skin cream composition is about 2.5 points higher than the pH of the night skin cream composition.

4. The skin care system of claim 1, further comprising a child-friendly bottle for each composition that can be used by young children without difficulty, wherein the bottle for the day composition comprises graphics indicating day-time use and the bottle for the night composition comprises graphics indicating night-time use.

5. A skin care method of using the system of claim 1, comprising:
  applying the day composition topically in the morning to a child between six months and eighteen years of age; and
  applying the night composition topically at night to the child.

6. The skin care method of claim 5, wherein applying the day composition comprises applying the day composition topically each day to the face after tooth-brushing, and applying the night composition comprises applying the night composition topically to the face each night after tooth-brushing.

* * * * *